United States Patent [19]
Bergsma et al.

[11] Patent Number: 6,008,012
[45] Date of Patent: Dec. 28, 1999

[54] HUMAN SOMATOSTATIN-LIKE RECEPTOR

[75] Inventors: Derk Jon Bergsma, Berwyn, Pa.; Catherine Elizabeth Ellis, Glassboro, N.J.

[73] Assignee: Smithkline Beecham Corporation,, Philadelphia, Pa.

[21] Appl. No.: 08/602,809

[22] PCT Filed: Dec. 15, 1995

[86] PCT No.: PCT/US95/16472

§ 371 Date: Jun. 13, 1997

§ 102(e) Date: Jun. 13, 1997

[87] PCT Pub. No.: WO96/18651

PCT Pub. Date: Jun. 20, 1996

[51] Int. Cl.$^6$ .......................... C07K 14/705; C12N 15/12
[52] U.S. Cl. .................. 435/69.1; 435/252.3; 435/320.1; 530/380; 536/23.5
[58] Field of Search ..................................... 435/7.1, 69.1, 435/252.7, 320.1; 530/350; 536/23.5

[56] References Cited

PUBLICATIONS

Kolakowski et al., "Characterization of a human gene related to genes encoding somatostatin receptors," *FEBS Letters* 398, pp. 253–258 (1996).

Rohrer et al., "Cloning and Characterization of a Fourth Human Somatostatin Receptor", *Proceedings of the National Academy of Science,* vol. 90, pp. 4196–4200 (1993).

Yamada et al., "Cloning and Functional Characterization of a Family of Human and Mouse Somatostatin Receptors Expressed in Brain, Gastrointestinal Tract and Kidney", *Proceedings of the National Academy of Science,* vol. 89, pp. 251–255 (1992).

*Primary Examiner*—John Ulm
*Attorney, Agent, or Firm*—William T. Han; Ratner & Prestia; William T. King

[57] ABSTRACT

This invention relates to a novel human somatostatin-like receptor, isolated nucleic acids encoding same, recombinant host cell transformed with an somatostatin-like receptor encoding DNA and to uses of the expressed receptor and nucleic acid sequences in drug screening and development as well as in therapeutic and diagnostic applications.

10 Claims, No Drawings

6,008,012

HUMAN SOMATOSTATIN-LIKE RECEPTOR

FIELD OF THE INVENTION

This invention relates to a novel human somatostatin-like receptor, isolated nucleic acids encoding same, recombinant host cell transformed with DNA encoding said receptor and to uses of the expressed receptor and nucleic acid sequences in drug screening and development as well as in therapeutic and diagnostic applications.

BACKGROUND OF THE INVENTION

Somatostatin (SST) is produced endogenously as two bioactive peptides which act on numerous target cells notably in the brain, pancreas, gastoinestinal tract, pituitary, adrenals and thyroid to regulate cell processes such sa neurotransmission, glandular secretion, smooth muscle contractility and cell proliferation (Reichlin, S., *N. Eng. J. Med.*, 309:1495–1501 and 1556–1563 (1983)). Thus somatostatin can function as a neurotransmitter as well as a hormone. Its hormonal effects include suppression of release of many pituitary, pancreatic and gastrointestinal hormones, e.g., human growth hormone. The cellular actions of somatostatin are mediated by cell surface receptors (SSTRs), which transduce their intracellular signals via G protein-coupled pathways.

Somatostatin binds to a family of structurally-related proteins. Presently there are five known somatostatin receptor subtypes,designated SSTR1-5 (Yamada et al., *Proc. Natl. Acad. Sci.*, 89:251–255 (1992), Yamada et al., *Biochem. Biophys. Res. Comm.*, 195:844–852 (1993) and Patel et al., *Biochem. Biophys. Res. Comm.*, 198:605–612 (1994)).

This invention thus provides a novel receptor of the human somatostatin subtype. The DNAs of this invention, such as the specific sequences disclosed herein, are useful in that they encode the genetic information required for expression of this novel class of somatostatin receptors. Additionally, the sequences may be used as probes in order to isolated and identify addition members of the family, type and/or subtype as well as forming the basis of antisense therapy for disease conditions which are characterized by atypical expression of the somatostatin gene. The novel protein is itself useful as a therapeutic, a diagnostic agent (e.g., antibodies that specifically bind to such protein), and as a component in a screening system for drugs which are antagonists or agonists of such receptor activity. These and additional uses for the reagents described herein will be come apparent to those of ordinary skill in the art upon reading this specification.

SUMMARY OF THE INVENTION

This invention provides isolated nucleic acid molecules encoding a human somatostatin-like receptor, including mRNAs, DNAs, cDNAs as well as antisense analogs thereof and biologically active and diagnostically or therapeutically useful fragments thereof.

This invention also provides recombinant vectors, such as cloning and expression plasmids useful as reagents in the recombinant production of human somatostatin-like proteins or peptides, as well as recombinant prokaryotic and/or eukaryotic host cells comprising human somatostatin-like nucleic acid sequence.

This invention also provides methods of identifying ligands capable of binding to human somatostatin-like receptors by measuring the binding of the ligand to be identified relative to known ligands.

This invention also provides a process for preparing a somatostatin receptor which comprises culturing recombinant prokaryotic and/or eukaryotic host cells, containing human somatostatin-like nucleic acid sequence, under conditions promoting expression of said receptor. Another related aspect of this invention is an isolated human somatostatin receptor protein and antibodies that are directed (i.e., bind) to the receptor protein of the instant invention.

This invention also provides methods for screening drugs to identify such drugs which interact with and bind to human somatostatin-like receptors. The receptors may be in isolated form (e.g., as a membrane preparation) or may be expressed on the surface of recombinant host cells. Regardless of the form of the receptor, a plurality of candidate drugs are contacted with the receptor under conditions sufficient to form a drug/receptor binding complex and drugs capable of forming, enhancing or interfering with said complexes are detected.

This invention also provides nucleic acid probes comprising nucleic acid molecules of sufficient length to specifically hybridize to human somatostatin-like sequences.

This invention also provides an antisense oligonucleotide having a sequence capable of binding with mRNAs encoding human somatostatin-like receptors so as to prevent the translation of said mRNA.

This invention also provides transgenic non-human animals comprising a nucleic acid molecule encoding a human somatostatin-like receptor. Also provided are methods for use of said transgenic animals as models for differential receptor expression, mutation and SAR evaluation as well as in ligand and drug screens.

This invention also provides method of screening compounds to identify those compounds which bind to a human somatostatin-like receptor comprising: providing a recombinant host cell expressing on the surface thereof a human somatostatin-like receptor, said receptor being associated with a second component capable of providing a detectable signal in response to the binding of a compound to said receptor, contacting a plurality of candidate compounds with said host cells under conditions sufficient to permit binding of compounds to the receptor; and identifying those compounds capable of receptor binding by detecting the signal produced by said second component.

This invention also provides a method for treating abnormalities which are related to excess human somatostatin-like receptor activity which comprises administering to a subject a pharmaceutical composition containing the antibody of the invention (or an antagonist of the invention) which is effective to block binding of naturally occurring ligands to said somatostatin-like receptor and thereby alleviating said abnormalities. Conversely, the invention also provides a method for treating conditions which are related to insufficient human somatostatin-like receptor activity which comprises administering to a subject a pharmaceutical composition containing an agonist of the invention which binds to said somatostatin-like receptor and thereby alleviating said conditions.

DETAILED DESCRIPTION OF THE INVENTION

This invention provides a human somatostatin-like receptor. The particular sequence identified as nucleotides 27 to 1232 of SEQ ID NO:1 herein represents one member the class.

In further describing the present invention, the following additional terms will be employed, and are intended to be defined as indicated below.

An "antigen" refers to a molecule containing one or more epitopes that will stimulate a host's immune system to make a humoral and/or cellular antigen-specific response. The term is also used herein interchangeably with "immunogen."

The term "epitope" refers to the site on an antigen or hapten to which a specific antibody molecule binds. The term is also used herein interchangeably with "antigenic determinant" or "antigenic determinant site."

A coding sequence is "operably linked to" another coding sequence when RNA polymerase will transcribe the two coding sequences into a single MRNA, which is then translated into a single polypeptide having amino acids derived from both coding sequences. The coding sequences need not be contiguous to one another so long as the expressed sequence is ultimately processed to produce the desire protein.

"Recombinant" polypeptides refer to polypeptides produced by recombinant DNA techniques; i.e., produced from cells transformed by an exogenous DNA construct encoding the desired polypeptide. "Synthetic" polypeptides are those prepared by chemical synthesis.

A "replicon" is any genetic element (e.g., plasmid, chromosome, virus) that functions as an autonomous unit of DNA replication in vivo; i.e., capable of replication under its own control.

A "vector" is a replicon, such as a plasmid, phage, or cosmid, to which another DNA segment may be attached so as to bring about the replication of the attached segment.

A DNA "coding sequence of" or a "nucleotide sequence encoding" a particular protein, is a DNA sequence which is transcribed and translated into a polypeptide when placed under the control of appropriate regulatory sequences.

A "promoter sequence" is a DNA regulatory region capable of binding RNA polymerase in a cell and initiating transcription of a downstream (3' direction) coding sequence. For purposes of defining the present invention, the promoter sequence is bound at the 3' terminus by a translation start codon (e.g., ATG) of a coding sequence and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

DNA "control sequences" refers collectively to promoter sequences, ribosome binding sites, polyadenylation signals, transcription termination sequences, upstream regulatory domains, enhancers, and the like, which collectively provide for the expression (i.e., the transcription and translation) of a coding sequence in a host cell.

A control sequence "directs the expression" of a coding sequence in a cell when RNA polymerase will bind the promoter sequence and transcribe the coding sequence into mRNA, which is then translated into the polypeptide encoded by the coding sequence.

A "host cell" is a cell which has been transformed or transfected, or is capable of transformation or transfection by an exogenous DNA sequence.

A cell has been "transformed" by exogenous DNA when such exogenous DNA has been introduced inside the cell membrane. Exogenous DNA may or may not be integrated (covalently linked) into chromosomal DNA making up the genome of the cell. In prokaryotes and yeasts, for example, the exogenous DNA may be maintained on an episomal element, such as a plasmid. With respect to eukaryotic cells, a stably transformed or transfected cell is one in which the exogenous DNA has become integrated into the chromosome so that it is inherited by daughter cells through chromosome replication. This stability is demonstrated by the ability of the eukaryotic cell to establish cell lines or clones comprised of a population of daughter cell containing the exogenous DNA.

A "clone" is a population of cells derived from a single cell or common ancestor by mitosis. A "cell line" is a clone of a primary cell that is capable of stable growth in vitro for many generations.

A "heterologous" region of a DNA construct is an identifiable segment of DNA within or attached to another DNA molecule that is not found in association with the other molecule in nature. Thus, when the heterologous region encodes a receptor gene, the gene will usually be flanked by DNA that does not flank the gene in the genome of the source animal. Another example of a heterologous coding sequence is a construct where the coding sequence itself is not found in nature (e.g., synthetic sequences having codons different from the native gene). Allelic variation or naturally occurring mutational events do not give rise to a heterologous region of DNA, as used herein.

This invention provides an isolated nucleic acid molecule encoding a human somatostatin-like receptor and substantially similar sequences. Isolated nucleic acid sequences are substantially similar if: (i) they are capable of hybridizing under moderately stringent conditions to nucleotides 27 to 1232 of SEQ ID NO:1; (ii) or they encode DNA sequences which are degenerate to nucleotides 27 to 1232 of SEQ ID NO:1. Degenerate DNA sequences encode the same amino acid sequence as nucleotides 27 to 1232 of SEQ ID NO:1, but have variation(s) in the nucleotide coding sequences. Hybridization under moderately stringent conditions is outlined in Example 1. Alternatively, substantially similar sequences are substantially the same when about 66% (preferably about 80%, more preferably 90%, and most preferably about 95%) of the nucleotides or amino acids match over a defined length of the molecule. As used herein, substantially similar refers to the sequences having similar identity to the sequences of the instant invention. Thus nucleotide sequences that are substantially the same can be identified by hybridization or by sequence comparison. Protein sequences that are substantially the same can be identified by one or more of the following: proteolytic digestion, gel electrophoresis and/or microsequencing.

One means for isolating a nucleic acid molecule encoding for a human somatostatin receptor is to probe a human genomic or cDNA library with a natural or artificially designed probe using art recognized procedures (See for example: "Current Protocols in Molecular Biology", Ausubel, F. M., et al. (eds.) Greene Publishing Assoc. and John Wiley Interscience, New York, 1989,1992). It is appreciated to one skilled in the art that SEQ ID NO:1, or fragments thereof comprising at least 15 contiguous nucleotides, is a particularly useful probe. Preferably, the probe is complementary to nucleotides 27 to 1232 of SEQ ID NO:1. Another particularly useful probe for this purpose is SEQ ID NO:3, or hybridizable fragments thereof (i.e., comprising at least 15 contiguous nucleotides). It is also appreciated that such probes can be and are preferably labeled with an analytically detectable reagent to facilitate identification of the probe. Useful reagents include but are not limited to radioactivity, fluorescent dyes or enzymes capable of catalyzing the formation of a detectable product. The probes are thus useful to isolate complementary copies of genomic DNA, cDNA or RNA from human, mammalian or other animal sources or to screen such sources for related sequences (e.g., additional members of the family, type and/or subtype) and including transcriptional regulatory and control elements defined above as well as other stability, processing, translation and tissue specificity-determining regions from 5' and/or 3' regions relative to the coding sequences disclosed herein.

This invention also provides for an isolated protein which is a human somatostatin-like receptor. This receptor is defined with reference to the amino acid sequence listed in SEQ ID NO:2 and includes variants with a substantially similar amino acid sequence that have the same receptor binding activity. The proteins of this invention are preferably made by recombinant genetic engineering techniques. The isolated nucleic acids particularly the DNAs can be introduced into expression vectors by operatively linking the DNA to the necessary expression control regions (e.g., regulatory regions) required for gene expression. The vectors can be introduced into the appropriate host cells such as prokaryotic (e.g., bacterial), or eukaryotic (e.g., yeast or mammalian) cells by methods well known in the art (Ausubel et al., supra). The coding sequences for the desired proteins having been prepared or isolated, can be cloned into any suitable vector or replicon. Numerous cloning vectors are known to those of skill in the art, and the selection of an appropriate cloning vector is a matter of choice. Examples of recombinant DNA vectors for cloning and host cells which they can transform include, but is not limited to, the bacteriophage λ (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillus subtilis*), pBD9 (Bacillus), pIJ61 (Streptomyces), pUC6 (Streptomyces), YIp5 (Saccharomyces), a baculovirus insect cell system, a Drosophila insect system, and YCp19 (Saccharomyces). See generally, "DNA Cloning": Vols. I & II, Glover et al. ed. IRL Press Oxford (1985) (1987) and; T. Maniatis et al. ("Molecular Cloning" Cold Spring Harbor Laboratory (1982).

The gene can be placed under the control of a promoter, ribosome binding site (for bacterial expression) and, optionally, an operator (collectively referred to herein as "control" elements), so that the DNA sequence encoding the desired protein is transcribed into RNA in the host cell transformed by a vector containing this expression construction. The coding sequence may or may not contain a signal peptide or leader sequence. The subunit antigens of the present invention can be expressed using, for example, the *E. coli* tac promoter or the protein A gene (spa) promoter and signal sequence. Leader sequences can be removed by the bacterial host in post-translational processing. e, e., U.S. Pat. Nos. 4,431,739; 4,425,437; 4,338,397.

In addition to control sequences, it may be desirable to add regulatory sequences which allow for regulation of the expression of the protein sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

An expression vector is constructed so that the particular coding sequence is located in the vector with the appropriate regulatory sequences, the positioning and orientation of the coding sequence with respect to the control sequences being such that the coding sequence is transcribed under the "control" of the control sequences (i.e., RNA polymerase which binds to the DNA molecule at the control sequences transcribes the coding sequence). Modification of the sequences encoding the particular antigen of interest may be desirable to achieve this end. For example, in some cases it may be necessary to modify the sequence so that it may be attached to the control sequences with the appropriate orientation; i.e., to maintain the reading frame. The control sequences and other regulatory sequences may be ligated to the coding sequence prior to insertion into a vector, such as the cloning vectors described above. Alternatively, the coding sequence can be cloned directly into an expression vector which already contains the control sequences and an appropriate restriction site.

In some cases, it may be desirable to produce mutants or analogs of the receptors of interest. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis, are well known to those skilled in the art. See, e.g., T. Maniatis et al., supra; *DNA Cloning*, Vols. I and II, supra; *Nucleic Acid Hybridization*, supra.

A number of prokaryotic expression vectors are known in the art. See, e.g., U.S. Pat. Nos. 4,578,355; 4,440,859; 4,436,815; 4,431,740; 4,431,739; 4,428,941; 4,425,437; 4,418,149; 4,411,994; 4,366,246; 4,342,832; see also U.K. Patent Applications GB 2,121,054; GB 2,008,123; GB 2,007,675; and European Patent Application 103,395. Yeast expression vectors are also known in the art See, e.g., U.S. Pat. Nos. 4,446,235; 4,443,539; 4,430,428; see also European Patent Applications 103,409; 100,561; 96,491. pSV2neo (as described in *J. Mol. Appl. Genet.* 1:327–341) which uses the SV40 late promoter to drive expression in mammalian cells or pCDNA1neo, a vector derived from pCDNA1 (*Mol. Cell Biol.* 7:4125–29) which uses the CMV promoter to drive expression. Both these latter two vectors can be employed for transient or stable (using G418 resistance) expression in mammalian cells. Insect cell expression systems, e.g., Drosophila, are also useful, see for example, PCT applications WO 90/06358 and WO 92/06212 as well as EP 290,261-B1.

Depending on the expression system and host selected, the proteins of the present invention are produced by growing host cells transformed by an expression vector described above under conditions whereby the protein of interest is expressed. If the expression system secretes the protein into growth media, the protein can be purified directly from the media. If the protein is not secreted, it is isolated from cell lysates or recovered from the cell membrane fraction. In the case, as here, were the protein is localized to the cell surface, whole cells or isolated membranes can be used as an assayable source of the desired gene producl The selection of the appropriate growth conditions and recovery methods are within the skill of the art.

An alternative method to identify proteins of the present invention is by constructing gene libraries, using the resulting clones to transform *E. coli* and pooling and screening individual colonies using polyclonal serum or monoclonal antibodies to the desired receptor.

The proteins of the present invention may also be produced by chemical synthesis such as solid phase peptide synthesis, using known amino acid sequences or amino acid sequences derived from the DNA sequence of the genes of interest. Such methods are known to those skilled in the art. Chemical synthesis of peptides is not particularly preferred.

The proteins of the present invention or their fragments comprising at least one epitope can be used to produce antibodies, both polyclonal and monoclonal. If polyclonal antibodies are desired, a selected mammal, (e.g., mouse, rabbit, goat, horse, etc.) is immunized with a receptor of the present invention, or its fragment, or a mutated receptor. Serum from the immunized animal is collected and treated according to known procedures. If serum containing polyclonal antibodies is used, the polyclonal antibodies can be purified by immunoaffinity chromatography or other known procedures.

Monoclonal antibodies to the proteins of the present invention, and to the fragments thereof, can also be readily produced by one skilled in the art. The general methodology for making monoclonal antibodies by using hybridoma technology is well known. Immortal antibody-producing cell lines can be created by cell fusion, and also by other techniques such as direct transformation of B lymphocytes with oncogenic DNA, or transfection with Epstein-Barr virus. See e.g., M. Schreier et al., "Hybridoma Techniques" (1980); Hammerling et al., "Monoclonal Antibodies and T-cell Hybridomas" (1981); Kennett et al., "Monoclonal Antibodies" (1980); see also U.S. Pat. Nos. 4,341,761; 4,399,121; 4,427,783; 4,444,887;,4,452,570; 4,466,917; 4,472,500; 4,491,632; and 4,493,890. Panels of monoclonal antibodies produced against the antigen of interest, or fragment thereof, can be screened for various properties; i.e., for isotype, epitope, affinity, etc. Monoclonal antibodies are useful in purification, using immnunoaffinity techniques, of the individual antigens which they are directed against. Alternatively, genes encoding the monoclonals of interest may be isolated from the hybridomas by PCR techniques known in the art and cloned and expressed in the appropriate vectors. The antibodies of this invention, whether polyclonal or monoclonal have additional utility in that they may be employed reagents in immunoassays, RIA, ELISA, and the like. As used herein, "monoclonal antibody" is understood to include antibodies derived from one species (e.g., murine, rabbit, goat, rat, human, etc.) as well as antibodies derived from two (or perhaps more) species (e.g., chimeric and humanized antibodies).

Chimeric antibodies, in which non-human variable regions are joined or fused to human constant regions (see, e.g. Liu et al., *Proc. Natl Acad. Sci. USA*, 84:3439 (1987)), may also be used in assays or therapeutically. Preferably, a therapeutic monoclonal antibody would be "humanized" as described in Jones et al., *Nature*, 321:522 (1986); Verhoeyen et al., *Science*, 239:1534 (1988); Kabat et al., *J Immunol.*, 147:1709 (1991); Queen et al., *Proc. Natl Acad. Sci. USA*, 86:10029 (1989); Gorman et al., *Proc. Natl Acad. Sci. USA*, 88:34181 (1991); and Hodgson et al., *Bio/Technology*, 9:421 (1991).

Therefore, this invention also contemplates antibodies, polyclonal or monoclonal (including chimeric and "humanized") directed to epitopes corresponding to amino acid sequences disclosed herein from the human somatostatin-like receptor. Particularly important regions of the receptor for immunological purposes are those hydrophilic region associated with extracellular domains of the receptor. Antibodies directed to the regions are particularly useful in diagnostic and therapeutic applications because of there effect upon receptor-ligand interaction. Methods for the production of polyclonal and monoclonal antibodies are well known, see for example Chap. 11 of Ausubel et al. (supra).

This invention also provides pharmaceutical compositions comprising an effective amount of antibody directed against the human somatostatin-like receptor to block binding of the naturally occurring ligands to that receptor in order to treat or ameliorate disease states associated with receptor activation. In its diagnostic embodiment the human somatostatin-like receptor on cell surfaces can be detected by contacting receptor bearing cells with antibodies of this invention and measuring the antibody/receptor complex. When the antibody is labeled with an analytically detectable reagent such a radioactivity, fluorescence, or an enzyme, the antibody can be use to detect the presence or absence of the receptor and/or its quantitative level.

This invention provides a method for determining whether a ligand previously not known to bind to a human somatostatin-like receptor can bind to such a receptor comprising contacting the ligand to be identified with a cell comprising the coding sequence of a human somatostatin-like receptor and expressing same on its surface under conditions sufficient for binding of ligands previously identified as binding to such a receptor. In other embodiments cell membrane fractions comprising the receptor may be used to measure binding of the ligand to be tested. When recombinant cells are used for purposes of expression of the receptor it is preferred to use cells with little or no endogenous receptor activity so that binding if any is due to the presence of the expressed receptor of interest. Preferred cells include human embryonic kidney cells, monkey kidney (HEK-293cells), fibroblast (COS) cells, Chinese hamster ovary (CHO) cells, Drosophila or murine L-cells. It is also preferred to employ as a host cell, one in which a receptor responsive second messenger system exists (i.e., "a second component capable of providing a detectable signal"). Well known second messenger systems include but are not limited to increases or decreases in phosphoinositide hydrolysis, adenylate cyclase, guanylate cyclase, or ion channel activity in response to ligand binding to extracellular receptor domains. In a further embodiment a specifically designed indicator of receptor binding can be constructed. For example a fusion protein can be made by fusing the receptor of this invention with a protein domain which is sensitive to receptor ligand binding. Such a domain referred to here as an indicator domain is capable, itself, or in association with accessory molecules, of generating an analytically detectable signal which is indicative of receptor ligand binding.

Alternatively, cell membrane preparations from transfected or transformed cells may be employed. In such a case binding of an analytically detectable ligand is measured. The use of radioactively labeled ligands is but one example of this invention. All of the above techniques that are useful for ligand identification are also useful in drug screening and drug development protocols.

In the compound screening embodiment of this invention, the human somatostatin-like receptor is isolated in a membrane fraction, or in cell bound form, and is contacted with a plurality of candidate molecules from which candidates are selected which bind to and interact with the receptor. The candidate compounds can be subjected to a competition screening assays, in which a known ligand, preferably labeled with an analytically detectable reagent, most preferably radioactivity, is introduced with the drug to be tested and the compound's capacity to inhibit or enhance the binding of the labeled ligand is measured. Alternatively, the binding or interaction can be measured directly by using radioactively labeled candidate compounds of interest or by the second messenger effect resulting from the interaction or binding of the candidate compounds. Compounds are screened for their increased affinity and selectivity to the receptor class of interest.

This invention also contemplates pharmaceutical compositions comprising compounds when identified by the above methods and a pharmaceutically acceptable carrier. Pharmaceutical compositions of proteineous drugs of this invention are particularly useful for parenteral administration, i.e., subcutaneously, intramuscularly or intravenously. The compositions for parenteral administration will commonly comprise a solution of the compounds of the invention or a cocktail thereof dissolved in an acceptable carrier, preferably an aqueous carrier. A variety of aqueous carriers may be employed, e.g., water, buffered water, 0.4% saline, 0.3% glycine, and the like. These solutions are sterile and generally free of particulate matter. These solutions may be sterilized by conventional, well known sterilization techniques. The compositions may contain pharmaceutically acceptable auxiliary substances as required to approximate physiological conditions such as pH adjusting and buffering agents, etc. The concentration of the compound of the invention in such pharmaceutical formulation can very widely, i.e., from less than about 0.5%, usually at or at least about 1% to as much as 15 or 20% by weight and will be selected primarily based on fluid volumes, viscosities, etc., according to the particular mode of administration selected.

Thus, a pharmaceutical composition of the invention for intramuscular injection could be prepared to contain 1 mL sterile buffered water, and 50 mg of a compound of the invention. Similarly, a pharmaceutical composition of the invention for intravenous infusion could be made up to contain 250 ml of sterile Ringer's solution, and 150 mg of a compound of the invention. Actual methods for preparing parenterally administrable compositions are well known or will be apparent to those skilled in the art and are described in more detail in, for example, *Remington's Pharmaceutical Science*, 15th ed., Mack Publishing Company, Easton, Pa.

The compounds described herein can be lyophilized for storage and reconstituted in a suitable carrier prior to use. This technique has been shown to be effective with conventional proteins and art-known lyophilization and reconstitution techniques can be employed.

In situations where the identified drug is non-proteineous, it may be administered alone or in combination with pharmaceutically acceptable carriers. The proportion of which is determined by the solubility and chemical nature of the compound, chosen route of administration and standard pharmaceutical practice. For example, they may be administered orally in the form of tablets or capsules containing such excipients as starch, milk sugar, certain types of clay and so forth. They may be administered sublingually in the form, of troches or lozenges in which the active ingredient is mixed with sugar and corn syrups, flavoring agents and dyes; and then. dehydrated sufficiently to make it suitable for pressing into a solid form. They may be administered orally in the form of solutions which may be injected parenterally, that is, intramuscularly, intravenously or subcutaneously. For parenteral administration they may be used in the form of a sterile solution containing other solutes, for example, enough saline or glucose to make the solution isotonic.

The physician will determine the dosage of the present therapeutic agents which will be most suitable and it will vary with the form of administration and the particular compound chosen, and furthermore, it will vary with the particular patient under patient under treatment. He will generally wish to initiate treatment with small dosages substantially less than the optimum dose of the compound and increase the dosage by small increments until the optimum effect under the circumstances is reached. It will generally be found that when the composition is administered orally, larger quantities of the active agent will be required to produce the same effect as a smaller quantity given parenterally. The compounds are useful in the same manner as other serotonergic agents and the dosage level is of the same order of magnitude as is generally employed with these other therapeutic agents. The therapeutic dosage will generally be from 1 to 10 milligrams per day and higher although it may be administered in several different dosage units. Tablets containing from 0.5 to 10 mg. of active agent are particularly useful.

Depending on the patient condition, the pharmaceutical composition of the invention can be administered for prophylactic and/or therapeutic treatments. In therapeutic application, compositions are administered to a patient already suffering from a disease in an amount sufficient to cure or at least partially arrest the disease and its complications. In prophylactic applications, compositions containing the present compounds or a cocktail thereof are administered to a patient not already in a disease state to enhance the patient's resistance.

Single or multiple administrations of the pharmaceutical compositions can be carried out with dose levels and pattern being selected by the treating physician. In any event, the pharmaceutical composition of the invention should provide a quantity of the compounds of the invention sufficient to effectively treat the patient.

Hence another aspect of this invention is a method for treating abnormalities which are related to excess human somatostatin-like receptor activity by administering an effective amount of a pharmaceutical composition containing compounds, identified by the methods of this invention, which are somatostatin-like receptor antagonists such that they block binding of naturally occurring ligands to the somatostatin receptor. Conversely, compounds identified by the methods of the invention, which are somatostatin-like receptor agonists, can be used for the treatment of conditions related to insufficient human somatostatin receptor activity by binding to said somnatostatin-like receptor and thereby alleviating said conditions.

This invention also contemplates, for example, using receptor encoding probes in the diagnostic evaluation of disease states characterized by an abnormal, if increased or decreased level of receptor gene expression. Alternatively, the probes can be used to identify individuals carrying chromosomal or molecular mutations in the gene encoding the receptor. Defining appropriate hybridization conditions is within the skill of the art. See, e.g., "Current Protocols in Mol. Biol." Vol. I & II, Wiley Interscience. Ausbel et al. (ed.) (1992). Probing technology is well known in the art and it is appreciated that the size of the probes can vary widely but it is preferred that the probe be at least 15 nucleotides in length. It is also appreciated that such probes can be and are preferably labeled with an analytically detectable reagent to facilitate identification of the probe. Useful reagents include but are not limited to radioactivity, fluorescent dyes or enzymes capable of catalyzing the formation of a detectable product. Hence depending on the conditions employed by the ordinary skilled artisan, the probes can be used to identify and recover additional examples of this receptor from other cell types and individuals. As a general rule the more stringent the hybridization conditions the more closely related genes will be that are recovered.

Also within the scope of this invention are antisense oligonucleotides predicated upon the sequences disclosed herein for the somatostatin-like receptor. Synthetic oligonucleotides or related antisense chemical structural analogs are designed to recognize and specifically bind to a target nucleic acid encoding the receptor gene and inhibit gene expression, e.g., the translation of the gene when the target nucleic acid is mRNA. Although not wishing to be bound to a particular theory for the mechanism of action of antisense drugs, it is believed that such drugs can act by one or more of the following mechanisms: by binding to mRNA and inducing degradation by endogenous nucleases such as RNase I or by inhibiting the translation of mRNA by binding to regulatory factors or ribosomal components necessary for productive protein synthesis. Additionally the antisense sequences can be use as components of a complex macromolecular arrays in which the sequences are combined with ribozyme sequences or reactive chemical groups and are used to specifically target mRNAs of interest and degrade or chemically modify said mRNAs. The general field of antisense technology is illustrated by the following disclosures which are incorporated herein by reference for purposes of background (Cohen, J. S., *Trends in Pharm. Sci.*, 10:435 (1989) and Weintraub, H. M. *Scientific American*, Jan. (1990) at page 40).

Transgenic, non-human, animals may be obtained by transfecting appropriate fertilized eggs or embryos of a host with nucleic acids encoding the human somatostatin-like receptor disclosed herein, see for example U.S. Pat. Nos. 4,736,866; 5,175,385; 5,175,384 and 5,175,386. The resultant transgenic animal may be used as a model for the study of receptor ligand interaction. Particularly, useful transgenic animals are those which display a detectable phenotype associated with the expression of the receptor. Drugs may then be screened for their ability to reverse or exacerbate the relevant phenotype. This invention also contemplates operatively linking the receptor coding gene to regulatory elements which are differentially responsive to various temperature or metabolic conditions, thereby effectively turning on or off the phenotypic expression in response to those conditions.

Although not necessarily limiting of this invention, following are some experimental data illustrative of this invention.

EXAMPLE I

Isolation of a Human Somatostatin-Like Receptor Gene:

A human cDNA library derived from the frontal cortex of the brain (Stratagene Inc., Cat. No. 936212)) was screened as described below using the coding region of an angiotensin II receptor type 1 ($AT_1$) gene (SEQ ID NO:3). The library was plated at approximately 20,000 pfus per plate and plaque lifts were done essentially as described by Sambrook, J et al., *In: Molecular Cloning: A Laboratory Manual.* Vol 1 2.108–2.116 (1989). Briefly, the plates were incubated overnight at 32° C., then nitrocellulose filters were placed over the plaques and subsequently "lifted off" where the plaques were denatured, neutralized and heated for 2 hours in a vacuum oven (80° C.). The nitrocellulose filters were prehybridized at 65° C. in a solution containing 6×SSPE, 5×Denhardt's solution (10 g Ficoll, 10 g BSA and 10 g Polyvinylpyrrolidone per liter solution), 0.05% SDS and 100 micrograms tRNA. The hybridization probes were radiolabelled using the Bios TAG-IT® kit. The filters were hybridized in the same prehybridization mix as above with the addition of dextran sulfate (10%) and the heat-denatured, radio-labeled DNA probes. The hybridization was carried out for approximately 18 hours at 65° C. (i.e., moderate stringent conditions). The filters were then washed in a solution of 2×SSC and 0.5% SDS at room temperature for 15 minutes (repeated once). The filters were then washed at 58° C., air-dried and exposed to X-ray film overnight at –70° C. with an intensifying screen. Following autoradiography plaques corresponding to positive signals were picked and subjected to several rounds of plaque purification. Recombinant phage clones were analyzed by Southern Blot and small hybridizing fragments subcloned for sequencing using an automated sequencer (Applied Biosystems Model 373A). Among the clones isolated in this screen was clone 11CB which was further characterized as described below.

Analysis of the Receptor Gene:

The original phage isolate was ≈1.3 kb in length. Sequence analysis of 11CB revealed it to be a novel gene belonging to the G-protein coupled receptor superfamily having homology to the published somatostatin receptor sequences (Yamada et al., *Proc. Nat'l. Acad. Sci.*, 89:251–255(1992), Yamada et al., *Biochem. Biophy. Res. Comm.*, 195 844–852 (1993)).

The open reading frame of 11CB specifies a protein of 402 amino acids and includes a stop codon (nucleotides 27–1235 of SEQ ID NO:1).

A comparison of the predicted amino acid sequence of 11CB to that of other G-protein coupled receptors shows that it shares strongest homology with the human somatostatin receptor (33% amino acid sequence identity and 55% nucleotide sequence (DNA) identity).

Heterologous Expression:

The 1.3 kb fragment containing the coding sequence can be subcloned into an expression vector either fused to another protein (e.g., operatively linked at the 5' end) or unfused to produce high levels of expression in transfected cells. Optionally the expression vector would encode a neomycin resistance gene to select for transfectants on the basis of ability to grow in G418 and a dihydrofolate reductase gene which permits amplification of the transfected gene in DHFR$^-$ cells. The plasmid can then be introduced into host cell lines e.g., CHO ACC98, a nonadherent, DHFR$^-$ cell line adapted to grow in serum free medium, and human embryonic kidney 293 cells (ATCC CRL 1573) and transfected cell lines can be selected by G418 resistance. Successful cell lines will express $5 \times 10^4 – 10^5$ sites per cell.

Compound Screening:

To identify novel, potent human somatostatin receptor agonists, compound screening is performed on whole cells, cell homogenates or cell membranes isolated from cell lines expressing the recombinant receptor of the instant invention. Activity of the compounds may be assessed using adenyl cyclase assays, since the receptor is believed to be negatively coupled to this second messenger system or assessed using phospholipase C assays (Martin et al., J. Biol. Chem., 258, 14816–14822 (1983) and incorporated by reference herein). Agonist potency and intrinsic activity is measured by the ability of the compound to inhibit forskolin-stimulated adenyl cyclase activity in either whole cells or membranes. Candidate compounds are then tested in animal models of therapeutic indications (e.g., as an adjunct to insulin therapy in the management of diabetes mellitus or antipoliferative effect on tumor cells (see Schally, A. V., *Cancer Res.*, 48:6977–6985 (1988))).

The above description and examples fully disclose the invention including preferred embodiments thereof. Those skilled in the art will recognize, or be able to ascertain using no more than routine experimentation, many equivalents to the specific embodiments herein. Such equivalents are intended to be within the scope of the following claims.

What is claimed is:

1. An isolated polynucleotide comprising a polynucleotide sequence which, by virtue of degeneracy of the genetic code, encodes the polypeptide sequence set forth in SEQ ID NO:2.

2. The isolated polynucleotide of claim 1 which is DNA.

3. The isolated polynucleotide of claim 1 which is RNA.

4. A vector comprising the isolated polynucleotide of claim 1.

5. The vector according to claim 4 which is a plasmid.

6. A recombinant host cell comprising the vector of claim 4.

7. A process for preparing a polypeptide having the amino acid sequence as set forth in SEQ ID NO:2 comprising culturing the recombinant host cell of claim 6 under conditions promoting expression of said polypeptide.

8. An isolated polypeptide comprising the amino acid sequence of SEQ ID NO:2.

9. An isolated polynucleotide comprising a nucleotide sequence set forth in nucleotides 27 to 1232 of SEQ ID NO:1.

10. An isolated polynucleotide which is complementary to nucleotides 27 to 1232 of SEQ ID NO:1 or to a polynucleotide which encodes the amino acid sequence of SEQ ID NO:2, said complementation being over the entire length of nucleotides 27 to 1232 of SEQ ID NO:1 or said encoding polynucleotide.

* * * * *

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
       (A) LENGTH: 1316 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:1:

```
GAATTCGGCA CGAGCAGGAG GCAGGCATGT TGTGTCCTTC CAAGACAGAT GGCTCAGGGC     60
ACTCTGGTAG GATTCACCAG GAAACTCATG GAGAAGGGAA AAGGGACAAG ATTAGCAACA    120
GTGAAGGGAG GGAGAATGGT GGGAGAGGAT TCCAGATGAA CGGTGGGTCG CTGGAGGCTG    180
AGCATGCCAG CAGGATGTCA GTTCTCAGAG CAAAGCCCAT GTCAAACAGC CAACGCTTGC    240
TCCTTCTGTG CCCAGGATCA CCTCCTCGCA CGGGGAGCAT CTCCTACATC AACATCATCA    300
TGCCTTCGGT GTTCGGCACC ATCTGCCTCC TGGGCATCAT CGGGAACTCC ACGGTCATCT    360
TCGCGGTCGT GAAGAAGTCC AAGCTGCACT GGTGCAACAA CGTCCCCGAC ATCTTCATCA    420
TCAACCTCTC GGTAGTAGAT CTCCTCTTTC TCCTGGGCAT GCCCTTCATG ATCCACCAGC    480
TCATGGGCAA TGGGGTGTGG CACTTTGGGG AGACCATGTG CACCCTCATC ACGGCCATGG    540
ATGCCAATAG TCAGTTCACC AGCACCTACA TCCTGACCGC CATGGCCATT GACCGCTACC    600
TGGCCACTGT CCACCCCATC TCTTCCACGA AGTTCCGGAA GCCCTCTGTG GCCACCCTGG    660
TGATCTGCCT CCTGTGGGCC CTCTCCTTCA TCAGCATCAC CCCTGTGTGG CTGTATGCCA    720
GACTCATCCC CTTCCCAGGA GGTGCAGTGG GCTGCGGCAT ACGCCTGCCC AACCCAGACA    780
CTGACCTCTA CTGGTTCACC CTGTACCAGT TTTTCCTGGC CTTTGCCCTG CCTTTTGTGG    840
TCATCACAGC CGCATACGTG AGGATCCTGC AGCGCATGAC GTCCTCAGTG GCCCCCGCCT    900
CCCAGCGCAG CATCCGGCTG CGGACAAAGA GGGTGACCCG CACAGCCATC GCCATCTGTC    960
TGGTCTTCTT TGTGTGCTGG GCACCCTACT ATGTGCTACA GCTGACCCAG TTGTCCATCA   1020
GCCGCCCGAC CCTCACCTTT GTCTACTTAT ACAATGCGGC CATCAGCTTG GGCTATGCCA   1080
ACAGCTGCCT CAACCCCTTT GTGTACATCG TGCTCTGTGA GACGTTCCGC AAACGCTTGG   1140
TCCTGTCGGT GAAGCCTGCA GCCCAGGGGC AGCTTCGCGC TGTCAGCAAC GCTCAGACGG   1200
CTGACGAGGA GAGGACAGAA AGCAAAGGCA CCTGATACTT CCCCTGCCAC CCTGCACACC   1260
TCCAAGTCAG GCACCACAA CACGCCACCG GGAGAGATGC TCTCGTGCCG AATTCC       1316
```

(2) INFORMATION FOR SEQ ID NO:2:

(i) SEQUENCE CHARACTERISTICS:
       (A) LENGTH: 402 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO:2:

```
Met Leu Cys Pro Ser Lys Thr Asp Gly Ser Gly His Ser Gly Arg Ile
  1               5                  10                  15
```

```
His Gln Glu Thr His Gly Glu Gly Lys Arg Asp Lys Ile Ser Asn Ser
            20                  25                  30
Glu Gly Arg Glu Asn Gly Gly Arg Gly Phe Gln Met Asn Gly Gly Ser
        35                  40                  45
Leu Glu Ala Glu His Ala Ser Arg Met Ser Val Leu Arg Ala Lys Pro
    50                  55                  60
Met Ser Asn Ser Gln Arg Leu Leu Leu Leu Cys Pro Gly Ser Pro Pro
65                  70                  75                  80
Arg Thr Gly Ser Ile Ser Tyr Ile Asn Ile Ile Met Pro Ser Val Phe
                85                  90                  95
Gly Thr Ile Cys Leu Leu Gly Ile Ile Gly Asn Ser Thr Val Ile Phe
            100                 105                 110
Ala Val Val Lys Lys Ser Lys Leu His Trp Cys Asn Asn Val Pro Asp
        115                 120                 125
Ile Phe Ile Ile Asn Leu Ser Val Val Asp Leu Leu Phe Leu Leu Gly
    130                 135                 140
Met Pro Phe Met Ile His Gln Leu Met Gly Asn Gly Val Trp His Phe
145                 150                 155                 160
Gly Glu Thr Met Cys Thr Leu Ile Thr Ala Met Asp Ala Asn Ser Gln
                165                 170                 175
Phe Thr Ser Thr Tyr Ile Leu Thr Ala Met Ala Ile Asp Arg Tyr Leu
            180                 185                 190
Ala Thr Val His Pro Ile Ser Ser Thr Lys Phe Arg Lys Pro Ser Val
        195                 200                 205
Ala Thr Leu Val Ile Cys Leu Leu Trp Ala Leu Ser Phe Ile Ser Ile
    210                 215                 220
Thr Pro Val Trp Leu Tyr Ala Arg Leu Ile Pro Phe Pro Gly Gly Ala
225                 230                 235                 240
Val Gly Cys Gly Ile Arg Leu Pro Asn Pro Asp Thr Asp Leu Tyr Trp
                245                 250                 255
Phe Thr Leu Tyr Gln Phe Phe Leu Ala Phe Ala Leu Pro Phe Val Val
            260                 265                 270
Ile Thr Ala Ala Tyr Val Arg Ile Leu Gln Arg Met Thr Ser Ser Val
        275                 280                 285
Ala Pro Ala Ser Gln Arg Ser Ile Arg Leu Arg Thr Lys Arg Val Thr
    290                 295                 300
Arg Thr Ala Ile Ala Ile Cys Leu Val Phe Phe Val Cys Trp Ala Pro
305                 310                 315                 320
Tyr Tyr Val Leu Gln Leu Thr Gln Leu Ser Ile Ser Arg Pro Thr Leu
                325                 330                 335
Thr Phe Val Tyr Leu Tyr Asn Ala Ala Ile Ser Leu Gly Tyr Ala Asn
            340                 345                 350
Ser Cys Leu Asn Pro Phe Val Tyr Ile Val Leu Cys Glu Thr Phe Arg
        355                 360                 365
Lys Arg Leu Val Leu Ser Val Lys Pro Ala Ala Gln Gly Gln Leu Arg
    370                 375                 380
Ala Val Ser Asn Ala Gln Thr Ala Asp Glu Glu Arg Thr Glu Ser Lys
385                 390                 395                 400
Gly Thr
```

(2) INFORMATION FOR SEQ ID NO:3:

(i) SEQUENCE CHARACTERISTICS:
        (A) LENGTH: 1080 base pairs
        (B) TYPE: nucleic acid (C) STRANDEDNESS: single
(D) TOPOLOGY: linear (ii) MOLECULE TYPE: cDNA (xi) SEQUENCE DESCRIPTION: SEQ ID NO:3:

| | | | | | | |
|---|---|---|---|---|---|---|
| ATGGCCCTTA | ACTCTTCTGC | TGAAGATGGT | ATCAAAAGAA | TCCAAGATGA | CTGCCCCAAG | 60 |
| GCTGGCAGGC | ACAGTTACAT | ATTTGTCATG | ATCCCTACCC | TCTACAGCAT | CATCTTTGTG | 120 |
| GTGGGAATAT | TTGGAAACAG | CTTGGTGGTC | ATTCTCATTT | ACTTTTACAT | GAAGCTGAAG | 180 |
| ACTGTGGCCA | GCGTCTTTCT | TCTCAATCTC | GCCTTGGCTG | ACTTATGCTT | TTTGCTGACT | 240 |
| TTGCCCCTGT | GGGCAGTCTA | TACCGCTATG | GAGTACCGCT | GGCCCTTCGG | CAATCACCTA | 300 |
| TGTAAGATCG | CTTCGGCCAG | CGTGAGCTTC | AACCTCTACG | CCAGTGTGTT | CCTTCTCACG | 360 |
| TGTCTCAGCA | TCGACCGCTA | CCTGGCCATC | GTCCACCCAA | TGAAGTCTCG | CCTTCGCCGC | 420 |
| ACGATGCTGG | TGGCCAAAGT | CACCTGCATC | ATCATCTGGC | TGATGGCTGG | CTTGGCCAGT | 480 |
| TTGCCAGCTG | TCATCCACCG | AAATGTATAC | TTCATCGAGA | ACACCAATAT | CACAGTGTGC | 540 |
| GCGTTTCATT | ATGAGTCTCG | GAATTCGACG | CTCCCCATAG | GGCTGGGCCT | TACCAAGAAT | 600 |
| ATTCTGGGCT | TCTTGTTCCC | TTTCCTTATC | ATTCTCACCA | GCTATACCCT | TATTTGGAAA | 660 |
| GCTCTAAAGA | AGGCTTATGA | AATTCAAAAG | AACAAACCAA | GAAACGATGA | CATCTTTAGG | 720 |
| ATAATTATGG | CGATTGTGCT | TTTCTTCTTC | TTTTCCTGGG | TCCCCCACCA | AATATTCACT | 780 |
| TTCCTGGATG | TGCTGATTCA | GCTGGGCGTC | ATCCATGACT | GTAAAATTTC | TGACATCGTG | 840 |
| GACACTGCCA | TGCCCATCAC | CATCTGCATA | GCGTATTTTA | ACAACTGCCT | GAACCCTCTG | 900 |
| TTCTACGGCT | TTCTGGGGAA | GAAATTTAAA | AAGTATTTCC | TCCAGCTCCT | GAAATATATT | 960 |
| CCCCCAAAGG | CCAAGTCCCA | CTCAAGCCTG | TCTACGAAAA | TGAGCACGCT | TTCTTACCGG | 1020 |
| CCTTCGGATA | ACATGAGCTC | ATCGGCCAAA | AAGCCTGCGT | CTTGTTTTGA | GGTGGAGTGA | 1080 |